(12) United States Patent
Balkovec et al.

(10) Patent No.: US 12,721,981 B2
(45) Date of Patent: Sep. 1, 2026

(54) APPARATUS AND METHOD FOR BIOLOGICAL TISSUE PUNCTURE EXPANSION

(71) Applicant: Boston Scientific Medical Device Limited, Galway (IE)

(72) Inventors: Christian Balkovec, Burlington (CA); Linus Hoi Che Leung, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 404 days.

(21) Appl. No.: 18/316,046

(22) Filed: May 11, 2023

(65) Prior Publication Data

US 2023/0364397 A1 Nov. 16, 2023

Related U.S. Application Data

(60) Provisional application No. 63/341,182, filed on May 12, 2022.

(51) Int. Cl.
*A61M 29/00* (2006.01)
*A61B 17/00* (2006.01)

(52) U.S. Cl.
CPC ... *A61M 29/00* (2013.01); *A61B 2017/00247* (2013.01); *A61M 2205/0266* (2013.01); *A61M 2207/00* (2013.01)

(58) Field of Classification Search
CPC .......... A61M 29/00; A61M 2205/0266; A61M 2207/00; A61M 25/0074; A61M 29/02; A61B 2017/00247; A61B 17/3478; A61B 2017/00243; A61B 2017/00986; A61B 17/3417
See application file for complete search history.

(56) References Cited

U.S. PATENT DOCUMENTS 5,707,362 A 1/1998 Yoon
5,836,913 A * 11/1998 Orth .................. A61B 17/3417 604/174

(Continued)

FOREIGN PATENT DOCUMENTS

CN 109107023 A 1/2019

OTHER PUBLICATIONS

International Search Report and Written Opinion issued in PCT/EP2023/062631, mailed Sep. 9, 2023.

(Continued)

*Primary Examiner* — Richard G Louis
(74) *Attorney, Agent, or Firm* — Nelson Mullins Riley & Scarborough LLP

(57) ABSTRACT

A method and apparatus are disclosed for an elongated introducer assembly. The elongated introducer assembly is manipulated and positioned proximate to a puncture hole in a tissue wall. A distal tip and distal end are advanced through the puncture hole and a distal expansion portion is selectively positioned relative to the puncture hole. An outer sliding shaft is advanced relative to an inner shaft, causing radial expansion of the distal expansion portion and an increase in outer diameter of the elongated introducer assembly at the distal expansion portion. Expansion of the puncture hole occurs as a result of the distal expansion portion in an expanded configuration passing through or spanning the puncture hole.

20 Claims, 18 Drawing Sheets

(56) References Cited

U.S. PATENT DOCUMENTS

| | | | | |
|---|---|---|---|---|
| 6,436,119 | B1 * | 8/2002 | Erb | A61B 17/3417 606/279 |
| 2001/0018596 | A1 * | 8/2001 | Selmon | A61M 29/02 606/198 |
| 2003/0181942 | A1 * | 9/2003 | Sutton | A61B 17/0057 606/200 |
| 2005/0043759 | A1 * | 2/2005 | Chanduszko | A61B 17/0057 606/213 |
| 2006/0063973 | A1 * | 3/2006 | Makower | A61B 17/282 600/114 |
| 2007/0208366 | A1 | 9/2007 | Pellegrino et al. | |
| 2011/0152760 | A1 * | 6/2011 | Parker | A61M 25/1006 623/1.11 |

OTHER PUBLICATIONS

Office Action received for European Application No. 23723214.5, mailed on Jun. 18, 2026, 8 pages.

* cited by examiner 122
120
128
140b
A
A
110
118
112
112
118
Section A:A

100

900
122
920
910
120
128
140b
130
112
110
118
126
124
100

APPARATUS AND METHOD FOR BIOLOGICAL TISSUE PUNCTURE EXPANSION

CROSS REFERENCE TO RELATED APPLICATION

This application claims the benefit of U.S. Provisional Patent Application No. 63/341,182, filed May 12, 2022, which is incorporated herein by reference in its entirety.

TECHNICAL FIELD

The disclosure relates to the apparatus and methods for selective expansion of a puncture hole in a tissue wall. More specifically, the apparatus is configured for selectively expanding a puncture site created in the fossa ovalis of the heart.

BACKGROUND OF THE INVENTION

Transseptal puncture is a procedure commonly performed when a physician needs to obtain access to left-sided chambers of the heart such as the left atrium or left ventricle. Venous vasculature is accessed percutaneously, and a catheter is used to facilitate delivery of a puncture device from the percutaneous access site to the fossa ovalis in the right atrium. The fossa ovalis is a thin flap of tissue that covers the foramen ovale, a remnant of the fetal heart and is an optimal site for puncture via a puncture device. Once an initial puncture hole in the tissue has been created, the puncture hole must be expanded to allow for the delivery of a therapy sheath through this site. As therapies continue to evolve in their complexity and capabilities, progressively larger therapy sheaths are required to cross the puncture hole made in the fossa ovalis. Known methods of expanding a puncture hole include the use of dilators that have a tapered distal end that progressively expands a puncture hole as the dilator is advanced across the fossa ovalis. Known dilators have larger outer diameters so that the puncture hole is expanded further to accommodate therapy sheaths with larger outer diameters. Dilators with larger outer diameters, however, can be more difficult to advance through a puncture hole as their distal end can only be gradually tapered over its length and, if too long, can potentially traumatize anatomical structures. Creating a shorter tapered end that must rapidly taper up to a larger outer diameter can be difficult, requiring a high force input to get the dilator across the puncture hole. Further, a larger fixed outer diameter will also expand the percutaneous access site which may be undesirable.

Known sheaths can expand their resting inner lumen size in response to a larger device being inserted through the inner lumen. The sheath is folded over onto itself in a resting configuration and unfurls to expand the inner lumen when a larger object is passed through. Unfortunately, the insertion of a larger object through the lumen of the known expandable sheath also expands the percutaneous access site, which may be undesirable. Further, this requires the introduction of another device into the patient vasculature via the expandable sheath lumen, increasing the risk for air embolism and/or thromboembolism.

Known basket catheters are commonly used with electro anatomical mapping systems. They have a distal end with splines that can be selectively deployed to enlarge the outer diameter of the distal end where the splines serve to facilitate efficient mapping of the heart via electrodes placed along the splines. The distal expansion can also be selectively reduced to accommodate smaller anatomical structures as well as removal of the device from a percutaneous access site. These basket catheters are complex to manufacture and typically feature the splines contained by a separate outer tubular member in addition to a separate inner tubular member. Further, the splines are flexible structures prone to bunching and designed to be atraumatic to anatomical structures as a user deliberately touches them against anatomical structures in the heart. Given this, the splines are not sufficiently robust to expand a tissue puncture hole.

Known balloon catheters have an inflatable balloon at the distal end of the device that can be used to expand a puncture hole such as balloon septostomy. The uninflated balloon section of the catheter is positioned across the puncture site and then the balloon is inflated, causing the puncture site to expand to the size of the inflated balloon. These devices are complex to manufacture, however, and it is difficult to selectively control the specific degree of inflation of the balloon, thereby making it difficult to selectively control the degree to which the puncture hole is expanded. Indiscriminate expansion of a puncture site can be deleterious to patient health; a puncture site, therefore, should only be expanded as far as it is required to for the requisite therapy sheath that must be subsequently inserted. Further, use of a balloon catheter requires an additional device to be inserted into the patient, increasing the risk for air embolism and/or thromboembolism. Therefore, there is a need for an apparatus and method for selectively expanding a puncture hole in a tissue wall while reducing device exchanges, procedural complexity, and time.

SUMMARY OF THE DISCLOSURE

In one broad aspect of the present disclosure, an elongated introducer assembly 100 comprises an outer sliding shaft 110 and an inner shaft 112. The elongated introducer assembly 100 is configured to be inserted into a patient 900 and positioned proximate to a tissue wall 910. A distal tip 122 is inserted through a puncture hole 920 in the tissue wall 910. A distal end 120 expands the puncture hole 920 until the distal end 120 protrudes from the puncture hole 920. The outer sliding shaft 110 is selectively advanced over the inner shaft 112, radially expanding a distal expansion portion which may take several forms as shown by differing elements 140, 140*a*, and 140*b* and that is contiguous with the outer sliding shaft 110, thereby increasing the outer diameter of the elongated introducer assembly 100 at the distal expansion portion 140, 140*a*, 140*b*. The distal expansion portion 140, 140*a*, 140*b* may be in an expanded configuration when the distal expansion portion 140, 140*a*, 140*b* is spanning the puncture hole 920, thereby selectively expanding the puncture hole 920. Alternatively, the elongated introducer assembly 100 may be retracted and/or advanced through the puncture hole 920, allowing passage of the distal expansion portion 140, 140*a*, 140*b* in an expanded configuration through the puncture hole 920, thereby selectively expanding the puncture hole 920. Following puncture hole 920 expansion, the outer sliding shaft 110 may be selectively retracted over the inner shaft 112, returning the distal expansion portion 140, 140*a*, 140*b* to a reduced expansion configuration.

In some examples, the elongated introducer assembly 100 further comprises a hollow lumen 118 extending along all or a portion of the length of the elongated introducer assembly 100 that may slidably receive a puncture device 200. The hollow lumen 118 may be centered or offset with respect to the cross-sectional profile of the elongated introducer assembly 100. When the distal tip 122 is proximate to the tissue wall 910, the puncture device 200 may be urged forward and advanced past the distal tip 122 to form a puncture hole 920 in the tissue wall 910. The puncture device 200 may be a sharp tipped needle, guidewire, radiofrequency electrode, or any combination thereof.

In some embodiments, the distal expansion portion 140, 140*a* of the elongated introducer assembly 100 comprises one or more distal buckling members 114 that are lower in stiffness than the outer sliding shaft 110. When the outer sliding shaft 110 is advanced over the inner shaft 112, the distal buckling members 114 buckle to a degree that is dependent on the relative amount of selective advancement of the outer shaft 110 relative to the inner shaft 112. This buckling results in a radial expansion of the elongated introducer assembly 100 at the distal expansion portion 140, 140*a* and a resultant increase in the outer diameter of the elongated introducer assembly 100 at the distal expansion portion 140, 140*a*. Retraction of the outer sliding shaft 110 relative to the inner shaft 112 from any selectively advanced state of the outer sliding shaft 110 relative to the inner shaft 112 will conversely reduce the degree of buckling at the distal buckling members 114 and cause a decrease in the outer diameter of the elongated introducer assembly 100 at the distal expansion portion 140, 140*a*.

In another embodiment, the distal expansion portion 140 comprises one or more expansion members 116 adjacent to one or more distal buckling members 114. The expansion member 116 is higher in stiffness compared to the distal buckling members 114 and may be positioned so that the expansion member 116 is spanning the puncture hole 920. The expansion member 116 may be a distal portion of the outer sliding shaft 110. When the outer sliding shaft 110 is advanced relative to the inner shaft 112, the expansion member 116 radially expands and causes expansion of the puncture hole 920 the expansion member 116 is spanning. Alternatively, the elongated introducer assembly 100 may be retracted and/or advanced through the puncture hole 920, allowing passage of the distal expansion portion 140 in an expanded configuration through the puncture hole 920, thereby selectively expanding the puncture hole 920.

In another embodiment, the distal expansion portion 140*b* comprises a pre-defined sloping geometry 128 on the inner shaft 112 and a distal portion of the outer sliding shaft 110. Advancement of the outer sliding shaft 110 causes a distal portion to traverse along the pre-defined sloping geometry 128, creating radial expansion of the distal expansion portion 140*b* of the elongated introducer assembly 100. The distal portion of the outer sliding shaft 110 that traverses along the pre-defined sloping geometry 128 of the inner shaft 112 may be configured into a plurality of split distal outer shaft segments 130 along the length of the outer sliding shaft 110. The split distal outer shaft segments 130 enable ready advancement over the pre-defined sloping geometry 128 and radial expansion of the distal expansion portion 140*b*.

In some examples, the outer sliding shaft 110 may be advanced by an outer sliding shaft advancer 126. The outer sliding shaft advancer 126 may be advanced and/or retracted along the elongated introducer assembly 100 via a button that is selectively depressed and released, enabling advancement and/or retraction of the outer sliding shaft 110 relative to the inner shaft 112 when depressed, and locking the position of the outer sliding shaft 110 when released. Further manner of advancement of the outer sliding shaft advancer 126 include a rotation-driven advancement, whereby rotation of the outer sliding shaft advancer 126 causes advancement and/or retraction of the outer sliding shaft 110 via a threaded pathway circumferential to the elongated introducer assembly 100. Yet another manner of advancement of the outer sliding shaft advancer 126 may include a frictional force that must be overcome when advancing and/or retracting the outer sliding shaft 110 relative to the inner shaft 112.

In some embodiments, indicators are positioned along the length of the elongated introducer assembly 100 that correspond to the outer diameter of the distal expansion portion 140, 140*a*, 140*b*. As the outer sliding shaft 110 is advanced relative to the inner shaft 112, the indicators correspond to the outer diameter of the distal expansion portion 140, 140*a*, 140*b* concomitant with the amount that the outer sliding shaft 110 has been advanced relative to the inner shaft 112.

In some embodiments, the elongated introducer assembly 100 includes a proximal hub 124 that may be gripped or handled when using the apparatus. The proximal hub 124 may include features such as a female luer connector, enabling attachment of known accessories such as syringes and/or hemostasis valves.

In another broad aspect of the present disclosure, a method for selective expansion of a puncture hole 920 in a tissue wall 910 is provided. The distal tip 122 of an elongated introducer assembly 100 is positioned proximate to a puncture hole 920 in a tissue wall 910. The distal tip 122 of the elongated introducer assembly 100 is then advanced through the puncture hole 920 followed by advancement of a distal end 120. A distal expansion portion 140, 140*a* is positioned until the distal expansion portion 140 spans the puncture hole 920 and then an outer shaft 110 is advanced over an inner shaft 112 on the elongated introducer assembly 100 causing expansion radially of the distal expansion portion 140, 140*a*.

In another aspect, the method includes positioning the distal tip 122 of the elongated introducer assembly 100 proximate to a tissue wall 910. A puncture device 200 is advanced through a hollow lumen 118 on the elongated introducer assembly 100 and protrudes from a distal tip 122 to create a puncture hole 920 in the tissue wall 910. Following the creation of the puncture hole 920 with a puncture device 200, the puncture hole 920 may be expanded with the method previously described.

In another aspect, the method includes radial expansion of the distal expansion portion 140, 140*a* prior to the distal expansion portion 140, 140*a* spanning the puncture hole 920. The elongated introducer assembly 100 may then be advanced through the puncture hole 920, causing further expansion of the puncture hole 920. The method may alternatively include expansion of the distal expansion portion 140, 140*a*, 140*b* after the distal expansion portion 140, 140*a*, 140*b* has fully traversed the puncture hole 920. The elongated introducer assembly 100 is then retracted through the puncture hole 920 causing further expansion of the puncture hole 920.

In some embodiments the elongated introducer assembly 100 has a proximal hub 124 comprising a female luer connector for connection of a syringe and/or hemostasis valve to facilitate injection and/or aspiration of fluid at any step of the method.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
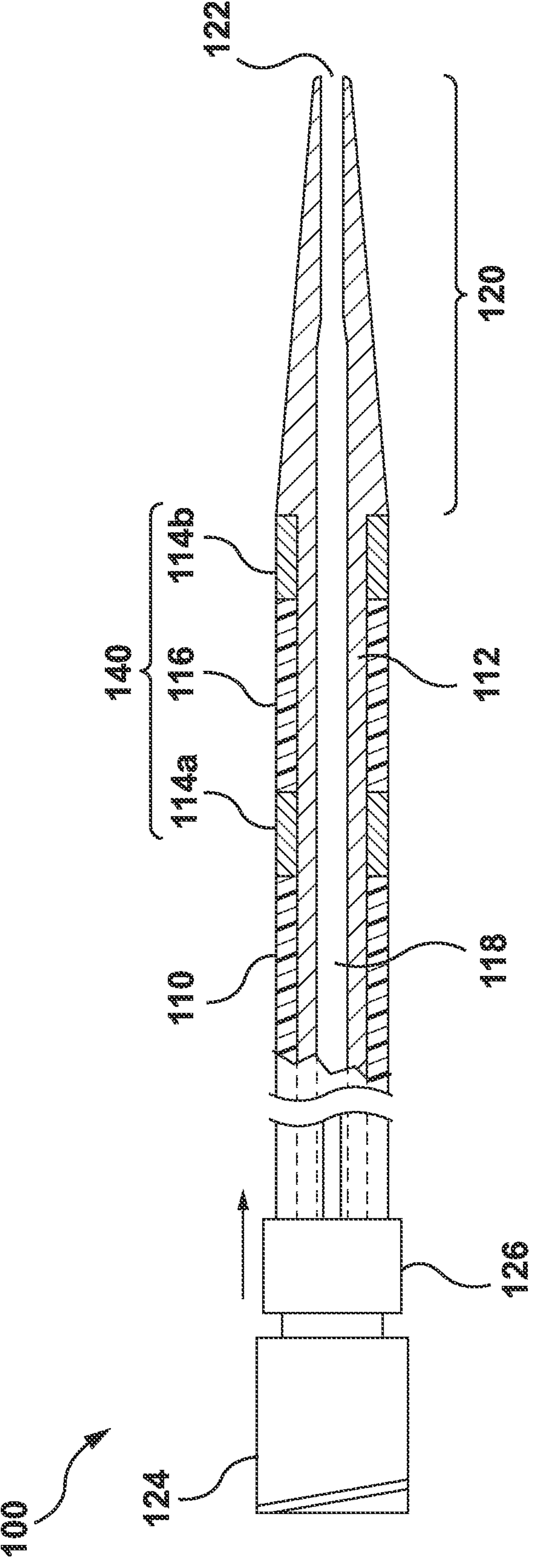
FIG. 1A depicts a partial cross section view of an elongated introducer assembly.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As further described hereinbelow, the present invention provides an apparatus and method for expansion of a puncture hole in a tissue wall. An elongated introducer assembly with a distal expansion portion is used to span a puncture hole and expand the puncture hole by way of advancement of an outer sliding shaft relative to an inner shaft on the elongated introducer assembly.

With reference to FIG. 1A, an elongated introducer assembly 100 is configured with a distal expansion portion 140. It should be understood that FIG. 1A is shown in partial cross-section, as are other partial cross-sections further described herein, such that the portion to the right of the wavy cut line is a cross-section while the portion to the left of the wavy cut line is not shown in cross-section. As well, the wavy cut line is provided to indicate that the length of the assembly 100 is variable. The outer diameter of the elongated introducer assembly 100 may be similar to other common percutaneous access devices used in the heart and have an outer diameter of approximately 7-8.5 Fr, however, any size is suitable that enables the device to be inserted percutaneously and through the intended vasculature to the heart. The overall length of the elongated introducer assembly 100 may be any length that facilitates device traversal through the intended vasculature to reach the target tissue in the heart; lengths of approximately 60-110 cm may be suitable. The distal expansion portion 140 is configured with a first distal buckling member 114*a*, an expansion member 116 and a second distal buckling member 114*b*. The elements comprising the distal expansion portion 140 are contiguous with an outer sliding shaft 110. The outer sliding shaft 110 is an elongate member that surrounds all or a portion of an inner shaft 112. The first distal buckling member 114*a* and second distal buckling member 114*b* are lower in mechanical stiffness than the outer sliding shaft 110 and the expansion member 116. Lower stiffness for the first distal buckling member 114*a* and second distal buckling member 114*b* may be achieved through use of materials that are lower in stiffness compared to the outer sliding shaft 110 and expansion member 116, removal of material that forms the buckling members, flattening of material that forms the buckling members, use of a smaller cross-sectional area for the buckling members, or any combination thereof. Any suitable biocompatible material may be used to create the first distal buckling member 114*a*, second distal buckling member 114*b*, outer sliding shaft 110, and inner shaft 112 such as stainless steel, nitinol, high density polyethylene (HDPE), low density polyethylene (LDPE), or any combination thereof. One suitable embodiment would provide that the outer sliding shaft 110 is fabricated from a high density polymer while the buckling members 114*a*, 114*b* are fabricated from a superelastic metal such as nitinol. The second distal buckling member 114*b* is rigidly fixed at its distal end to the inner shaft 112. The manner of affixing the second distal buckling member 114*b* may be facilitated by adhesives, welding, reflow, use of a fastener, or any suitable combination thereof. The expansion member 116 may be at least 1 mm in length so that the expansion member 116 may fully span the thickness of the tissue wall 910, but any length is suitable that accommodates the desired expansion. The expansion member 116 may be made of any suitable material and is stiffer than the first distal buckling section 114*a* or second distal buckling section 114*b*.

Still with reference to FIG. 1A, a distal end 120 terminating in a distal tip 122 comprises the elongated introducer assembly 100 distally. The distal tip 122 may have an outer diameter between 0.035" to 0.060", but any diameter that is able to be inserted through the required biological tissue is suitable. From the distal tip, the distal end 120 may gradually taper up in outer diameter to match the outer diameter of the remainder of the section comprising the outer sliding shaft 110 and distal expansion portion 140. The elongated introducer assembly 100 may have a hollow lumen 118 extending along all or a portion of the length of the elongated introducer assembly 100. The hollow lumen may be used for injection and/or aspiration of fluids and insertion of accessory devices such as guidewires and/or needles. The hollow lumen 118 may be centered or offset with respect to the cross-sectional profile of the elongated introducer assembly 100 with a diameter of 0.032" to 0.060", but any diameter that facilitates insertion of desired accessory devices is suitable. A proximal hub 124 may be situated proximally on the elongated introducer assembly 100 and provide a user with a location to grip during use. The proximal hub 124 may also incorporate a female luer connector (known and not depicted) to facilitate connection of luer-compatible devices such as syringes and/or hemostasis valves (known and not depicted). Along the length of the elongated introducer assembly 100 is an outer sliding shaft advancer 126 that is used to advance the outer sliding shaft 110 with respect to the inner shaft 112. The outer sliding shaft advancer 126 may be actuated in any suitable manner. For example, the sliding shaft advancer 126 may be advanced and/or retracted along the elongated introducer assembly 100 via a button (not shown) that is selectively depressed and released, enabling advancement and/or retraction of the outer sliding shaft 110 relative to the inner shaft 112 when depressed and locking the position of the outer sliding shaft 110 when released. Further manner of advancement of the outer sliding shaft advancer 126 may include a rotation-driven advancement (not shown) whereby rotation of the outer sliding shaft advancer 126 causes advancement and/or retraction of the outer sliding shaft 110 via a threaded pathway circumferential to the elongated introducer assembly 100. Yet another manner of advancement of the outer sliding shaft advancer 126 may include a frictional force (not shown) that must be overcome when advancing and/or retracting the outer sliding shaft 110 relative to the inner shaft 112.

Figure 1B:
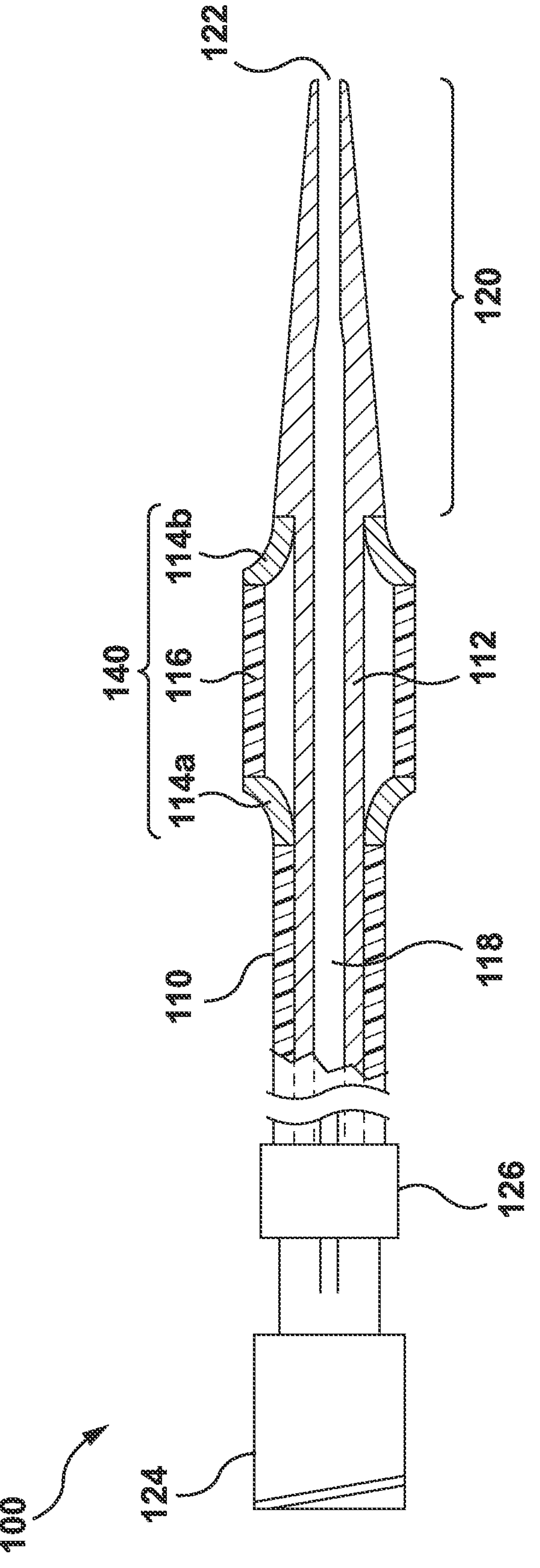
FIG. 1B depicts a partial cross section view of an elongated introducer assembly with an expanded distal expansion portion.

With reference to FIG. 1B, the same embodiment is shown as in FIG. 1A though now shown in an actuated position whereby the distal expansion portion 140 is radially displaced outwardly. The outer sliding shaft 110 is advanced over the inner shaft 112 via the outer sliding shaft advancer 126. Advancement of the outer sliding shaft 110 results in buckling at the first distal buckling member 114*a* and second distal buckling member 114*b* which elevates (i.e., radially displaces) the expansion member 116 from the surface of the inner shaft 112. Elevation of the expansion member 116 from the surface of the inner shaft 112 creates radial expansion of the elongated introducer assembly 100 at the distal expansion portion 140. Indicators may be positioned along the length of the elongated introducer assembly 100 that correlate to the thus radially expanded outer diameter of the distal expansion portion 140. As the outer sliding shaft 110 is advanced relative to the inner shaft 112, the indicators correspond to the outer diameter of the distal expansion portion 140 concomitant with the amount that the outer sliding shaft 110 has been advanced relative to the inner shaft 112. The distal expansion portion 140 when expanded, may have an outer diameter from 8.5-20 Fr, however, any desired outer diameter that offers suitable expansion for the intended application is suitable.

Figure 2A:
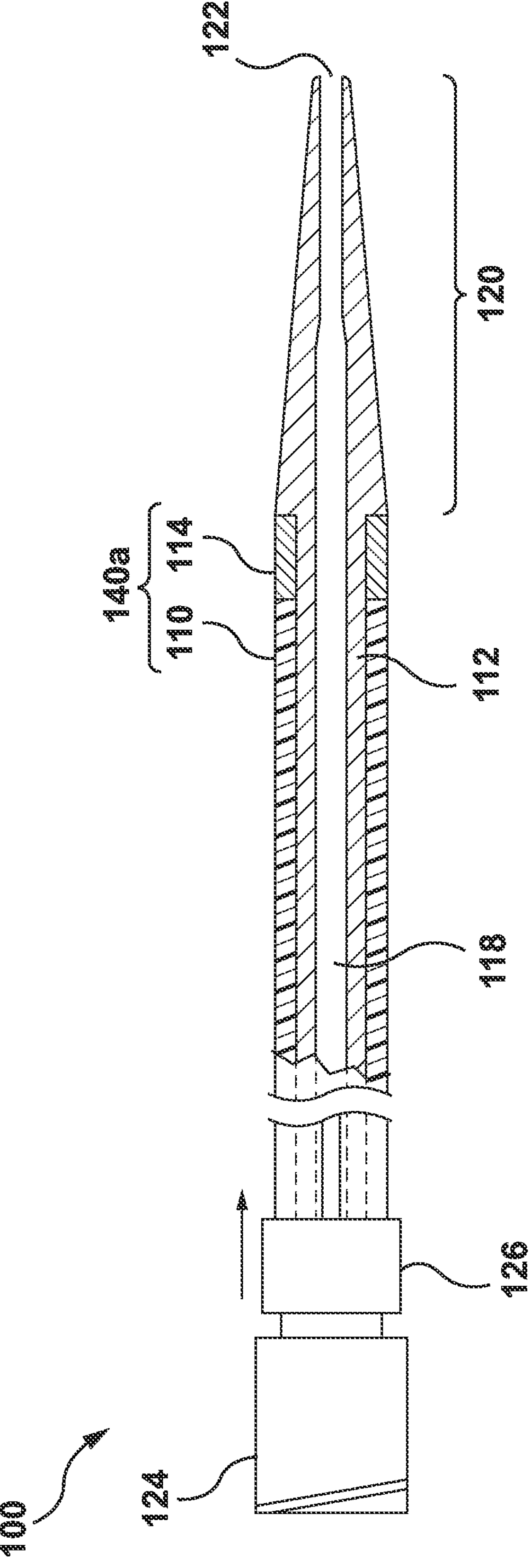
FIG. 2A depicts a partial cross section view of an elongated introducer assembly.

With reference to FIG. 2A, an alternative embodiment of an elongated introducer assembly 100 is shown. The distal expansion portion 140*a* includes a distal buckling member 114 and a distal portion of the outer sliding shaft 110. The distal buckling member 114 is rigidly fixed at the distal end of the distal buckling member 114 to the inner shaft 112. Affixing the distal buckling member 114 may be facilitated by adhesives, welding, reflow, use of a fastener, or any combination thereof.

Figure 2B:
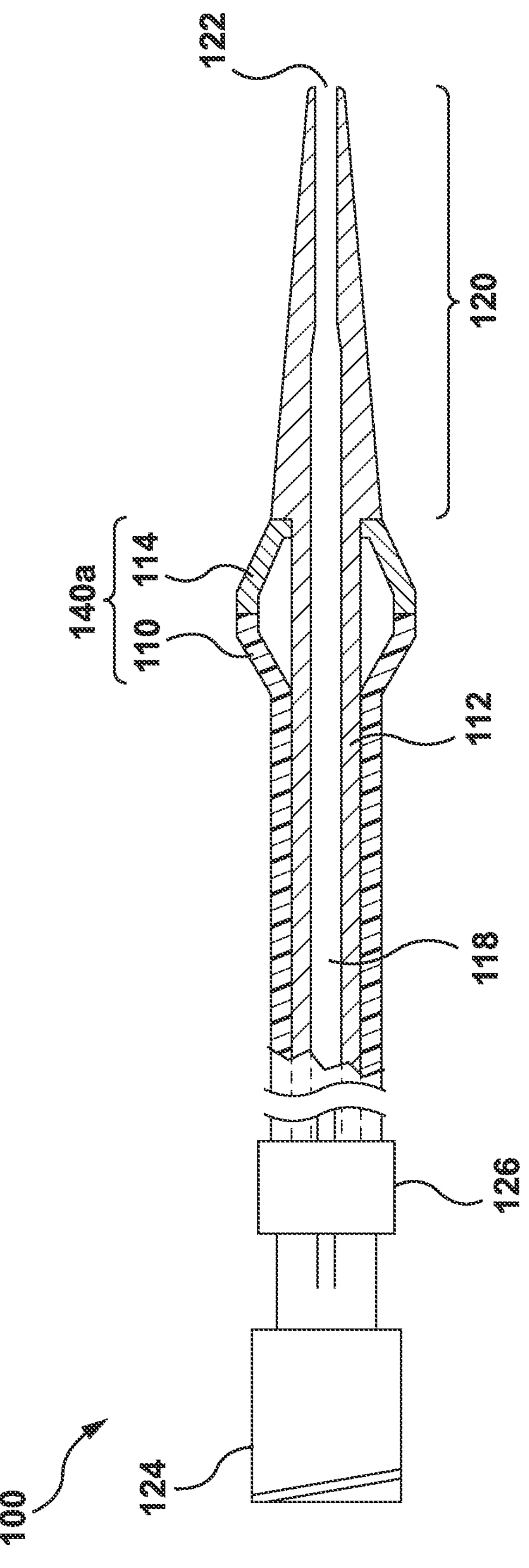
FIG. 2B depicts a partial cross section view of an elongated introducer assembly with an expanded distal expansion portion.

With reference to FIG. 2B, the same embodiment is shown as in FIG. 2A though now shown in an actuated position whereby the distal expansion portion 140*a* is radially displaced outwardly. The outer sliding shaft 110 is advanced over the inner shaft 112 via the outer sliding shaft advancer 126. Advancement of the outer sliding shaft 110 results in buckling at the distal buckling member 114 and a distal portion of the outer sliding shaft 110. This buckling creates radial expansion of the distal expansion portion 140*a* and an increase in the outer diameter of the elongated introducer assembly 100 at the distal expansion portion 140*a*.

Figure 3A:
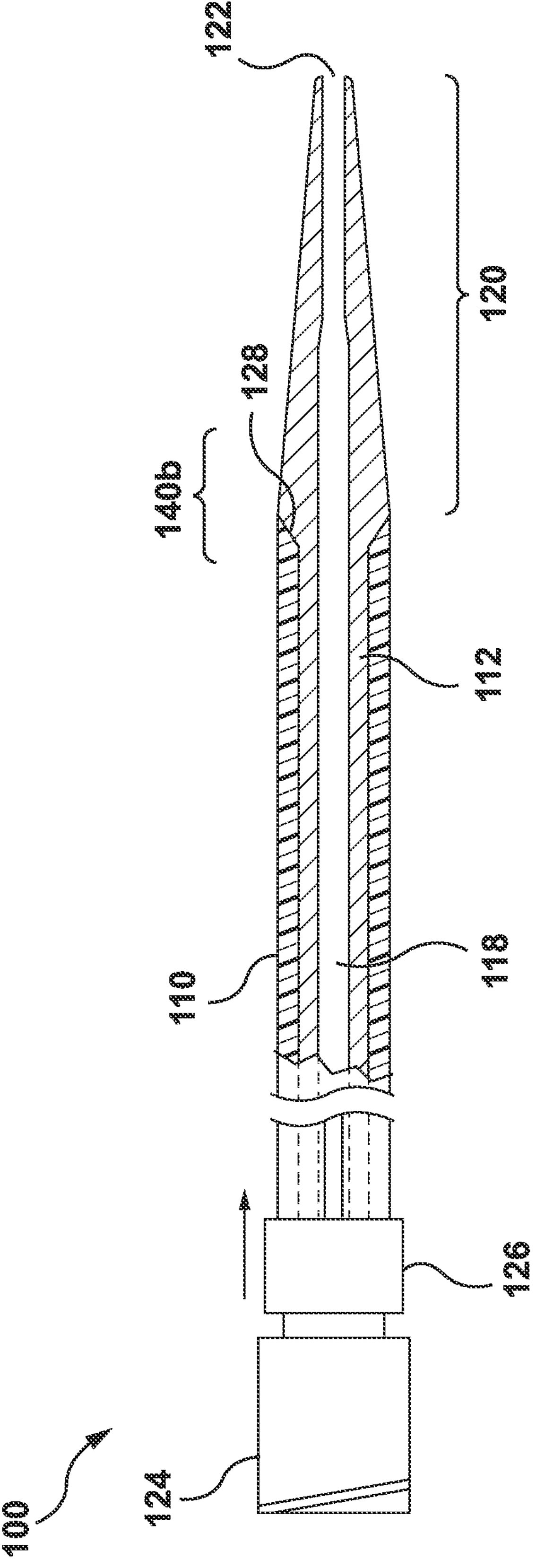
FIG. 3A depicts a partial cross section view of an elongated introducer assembly.

With reference to FIG. 3A, an alternative embodiment of an elongated introducer assembly 100 is shown. The distal expansion portion 140*b* includes a distal portion of the outer sliding shaft 110 and a pre-defined sloping geometry 128 on the inner shaft 112.

Figure 3B:
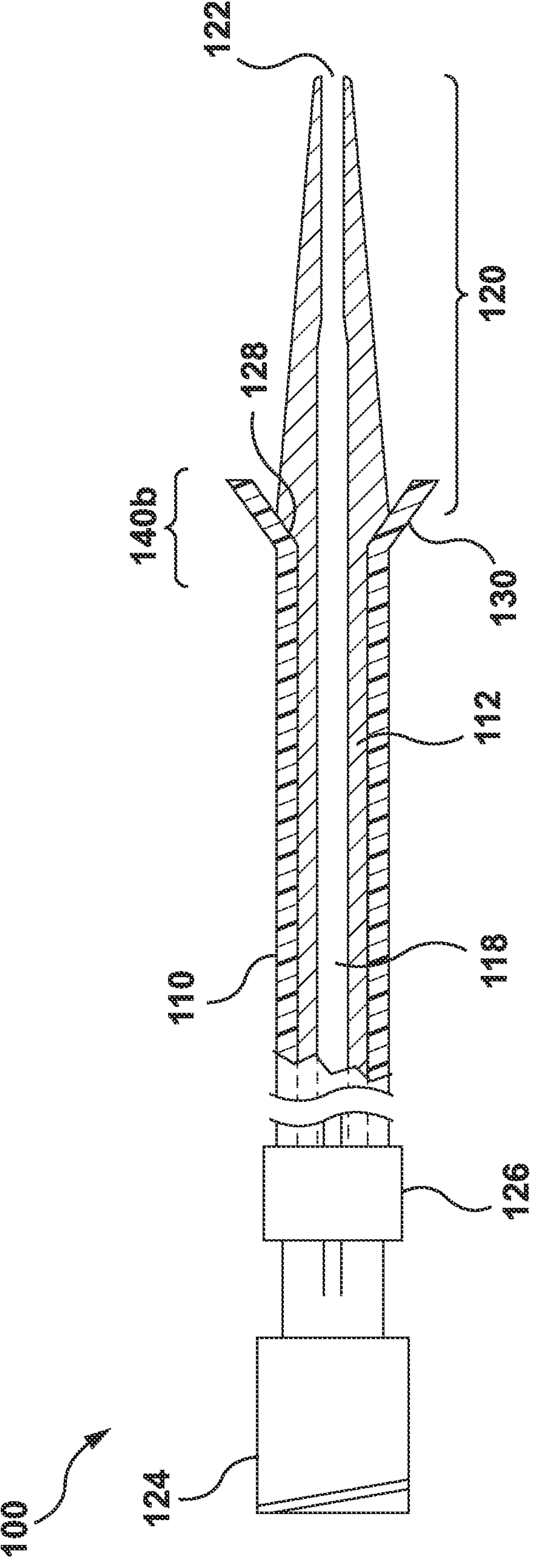
FIG. 3B depicts a cross section view of an elongated introducer assembly with an expanded distal expansion portion.

With reference to FIG. 3B, the same embodiment is shown as in FIG. 3A though now shown in an actuated position whereby the distal expansion portion 140*b* is radially displaced outwardly. The outer sliding shaft 110 is advanced via the outer sliding shaft advancer 126. A distal portion of the outer sliding shaft 110 traverses along the pre-defined sloping geometry 128, thereby creating radial expansion of the distal expansion portion 140*b* of the elongated introducer assembly 100. The radial expansion of the distal expansion portion 140*b* increases the outer diameter of the elongated introducer assembly 100 at the distal expansion portion 140*b*. The portion of the outer sliding shaft 110 that traverses along the pre-defined sloping geometry during advancement of the outer sliding shaft 110 relative to the inner shaft 112 may be the same material or a different material as the remainder of the outer sliding shaft 110. Further, the distal portion of the outer sliding shaft that is part of the distal expansion portion 140*b* may also have a different cross-sectional area than the remainder of the outer sliding shaft 110.

Figure 3C:
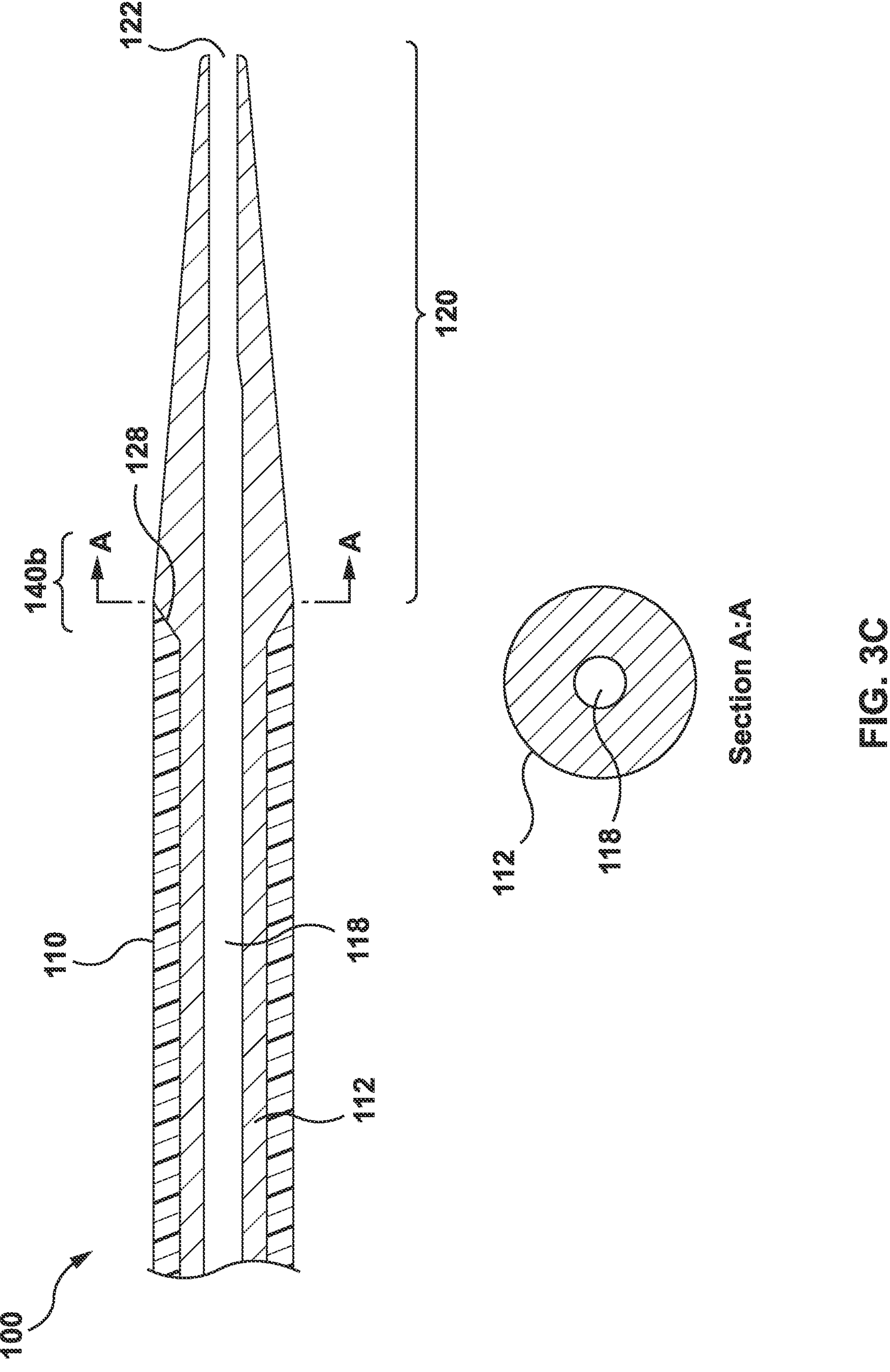
FIG. 3C depicts a cross section view of an elongated introducer assembly and a section view of a distal expansion portion.

With reference to FIG. 3C, the same embodiment is shown as in FIG. 3A. A section view of the distal expansion portion 140*b* is shown. In this configuration, the outer sliding shaft 110 is fully retracted relative to the inner shaft 112.

Figure 3D:
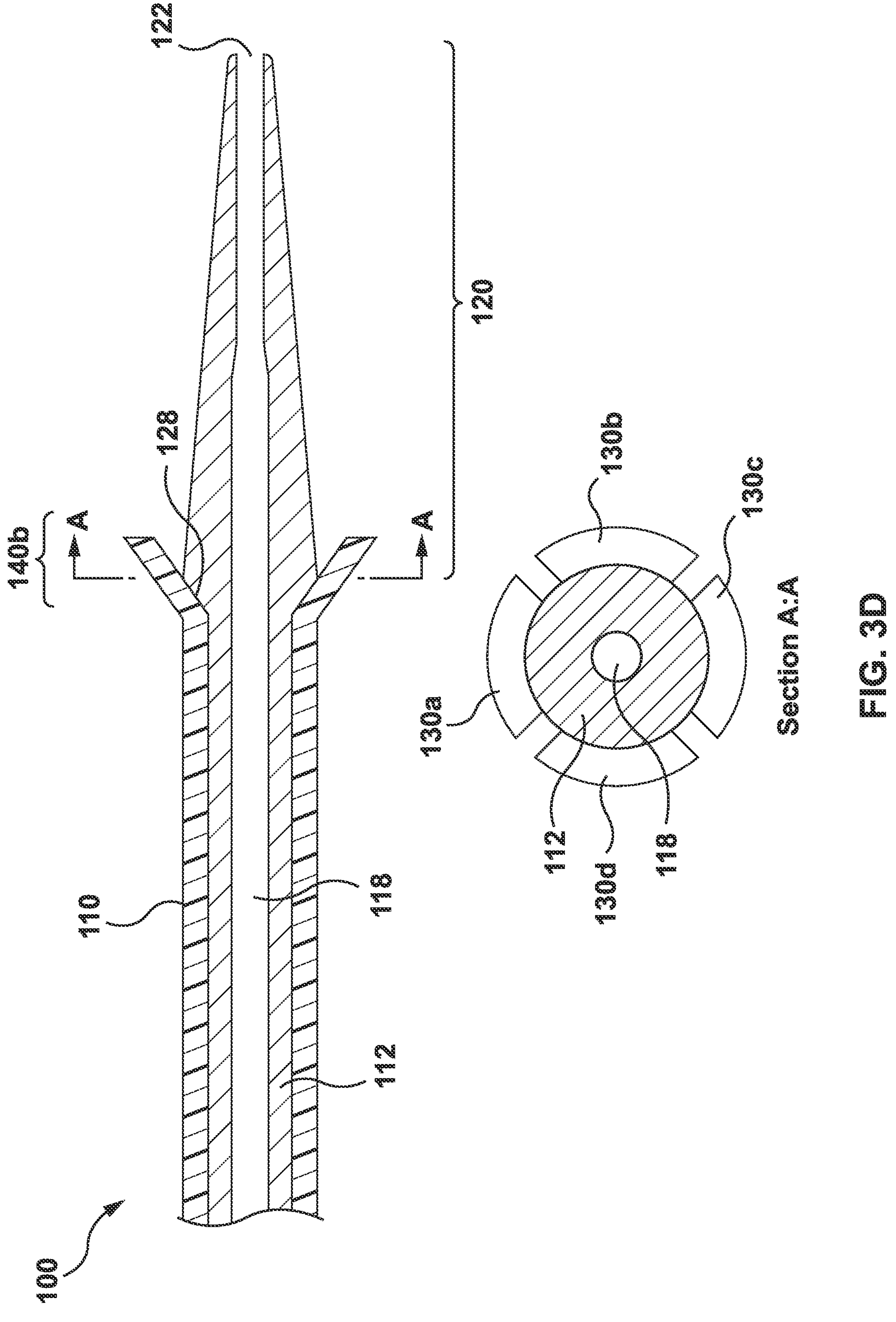
FIG. 3D depicts a cross section view of an elongated introducer assembly and a section view of an expanded distal expansion portion.

With reference to FIG. 3D, the same embodiment is shown as in FIG. 3A though now shown in an actuated position whereby the distal expansion portion 140*b* is radially displaced outwardly. A section view of the distal expansion portion 140*b* is shown. In this configuration, the outer sliding shaft 110 has been advanced relative to the inner shaft 112. The section view depicts a plurality of split distal outer shaft segments 130*a*, 130*b*, 130*c*, 130*d* along the length of the outer sliding shaft 110. The split distal outer shaft segments 130*a*, 130*b*, 130*c*, 130*d* are sections of the outer sliding shaft 110 that have been separated along the length of the outer sliding shaft 110 to enable ready advancement over the pre-defined sloping geometry 128 and radial expansion of the distal expansion portion 140*b*. The split distal outer shaft segments 130*a*, 130*b*, 130*c*, 130*d* are contiguous with the outer sliding shaft 110 and may be the same or a different material as the remainder of the outer sliding shaft 110. The split distal outer shaft segments 130*a*, 130*b*, 130*c*, 130*d* may also have a different cross-sectional area than the remainder of the outer sliding shaft 110. Any number of split distal outer shaft segments 130 may be used and they may be split for any length along the outer sliding shaft 110.

Figure 4A:
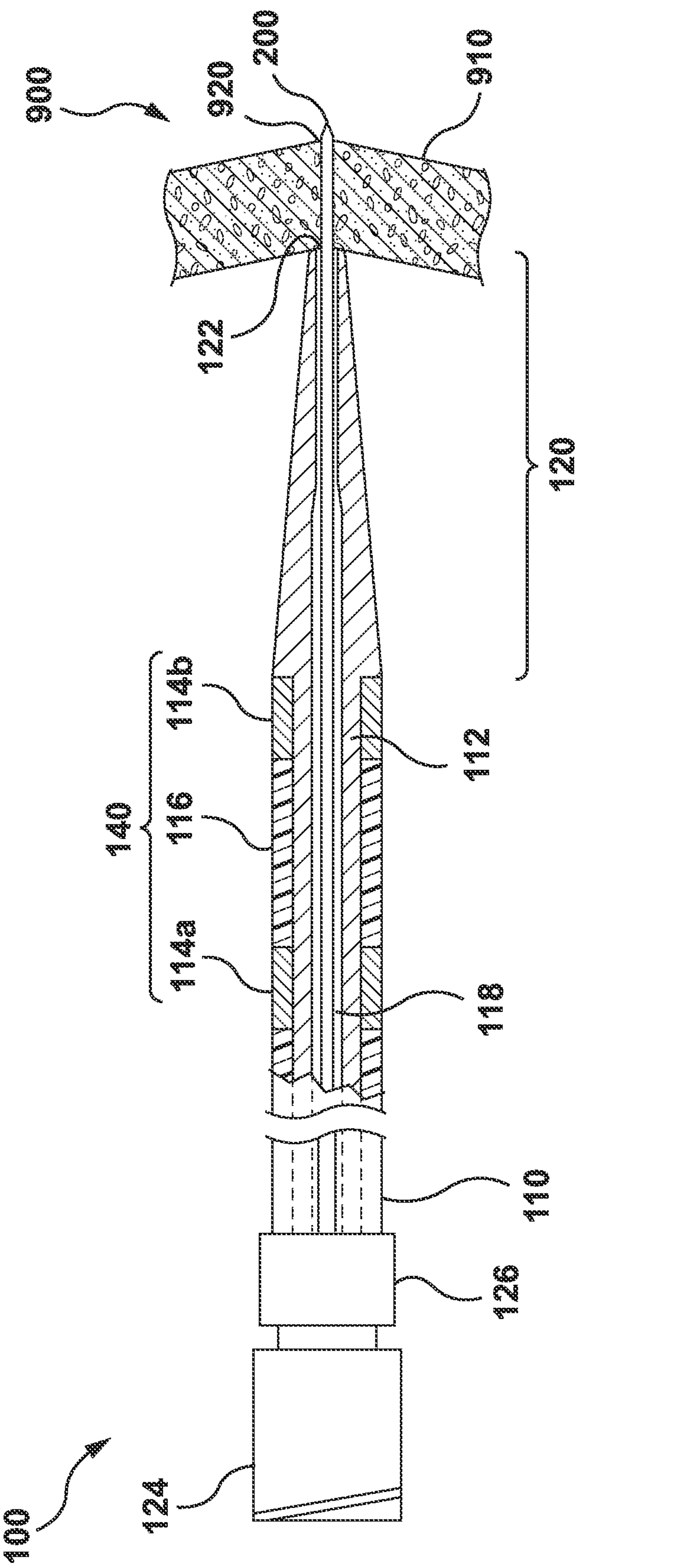
FIG. 4A depicts a partial cross section view of an elongated introducer assembly positioned proximate to a puncture hole in a tissue wall.

With reference to FIG. 4A, the same embodiment is shown as in FIG. 1A. The distal tip 122 of the elongated introducer assembly 100 is positioned proximate to a puncture hole 920 in a tissue wall 910 of a patient 900. A puncture device 200 is urged forward through the hollow lumen 118 past the distal tip 122 and is used to create the puncture hole 920.

Figure 4B:
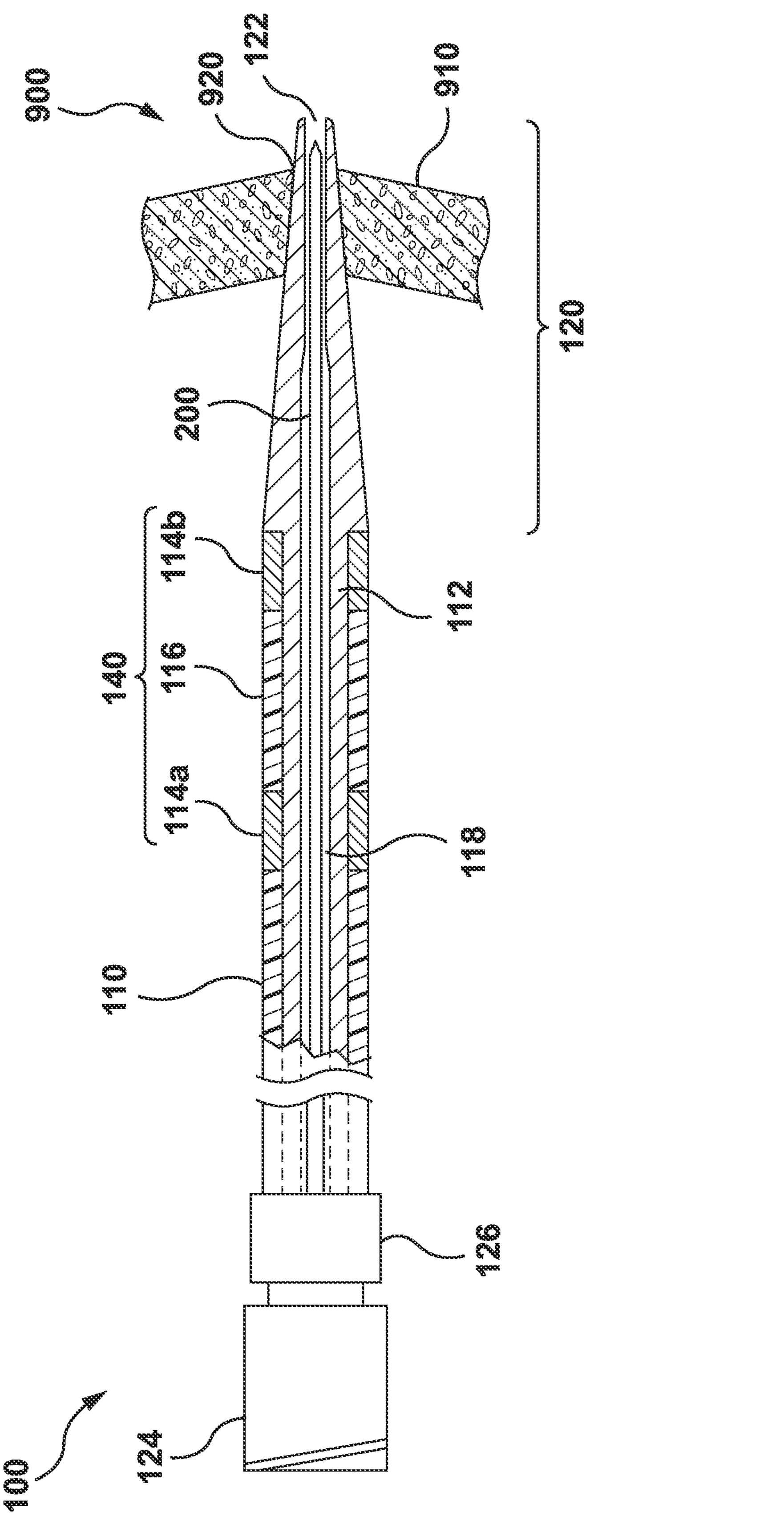
FIG. 4B depicts a partial cross section view of an elongated introducer assembly with a distal tip protruding through a puncture hole in a tissue wall.

With reference to FIG. 4B, the same embodiment is shown as in FIG. 1A, and a procedural continuation from FIG. 4A is shown. The distal tip 122 is advanced through the puncture hole 920 in the tissue wall 910 and the distal end 120 begins to traverse through the puncture hole 920 and gradually expands the diameter of the puncture hole 920 as the distal end 120 is further advanced through the puncture hole 920 and the taper of the distal end 120 expands proximally.

Figure 4C:
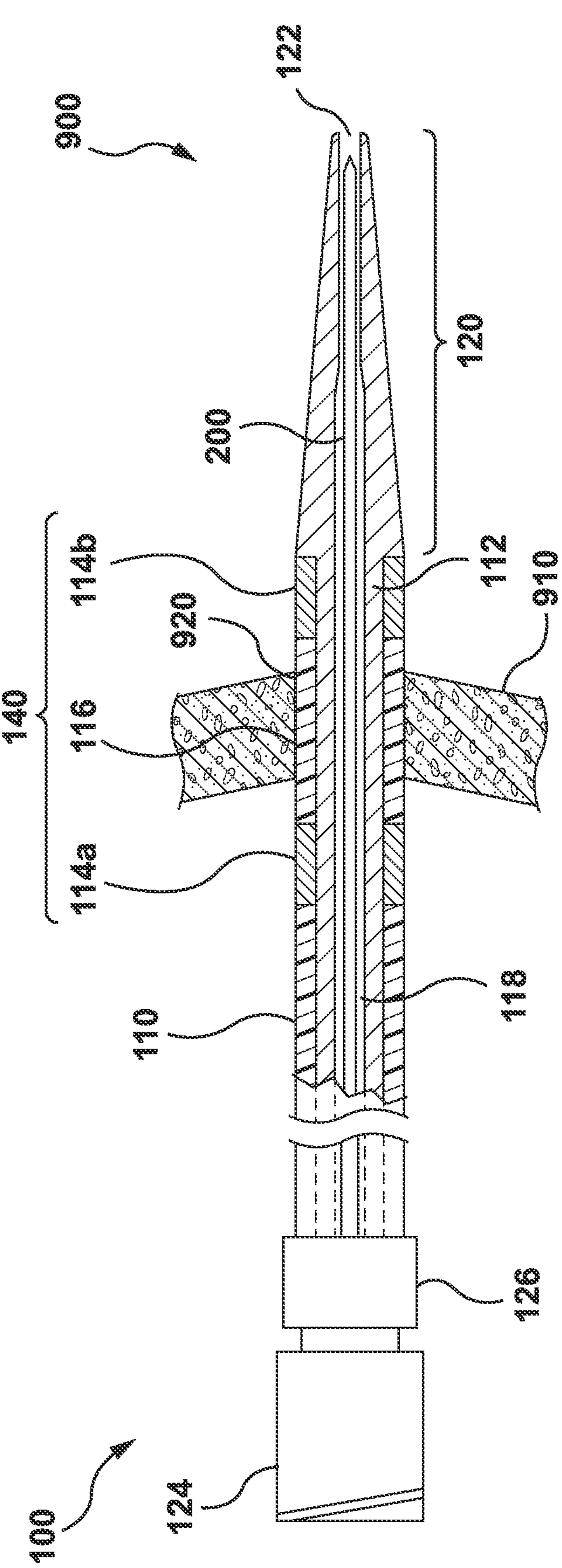
FIG. 4C depicts a partial cross section view of an elongated introducer assembly with an expansion member spanning a puncture hole in a tissue wall.

With reference to FIG. 4C, the same embodiment is shown as in FIG. 1A, and a procedural continuation from FIG. 4B is shown. The distal end 120 is fully advanced through the puncture hole 920 in the tissue wall 910 and the expansion member 116 spans the puncture hole 920.

Figure 4D:
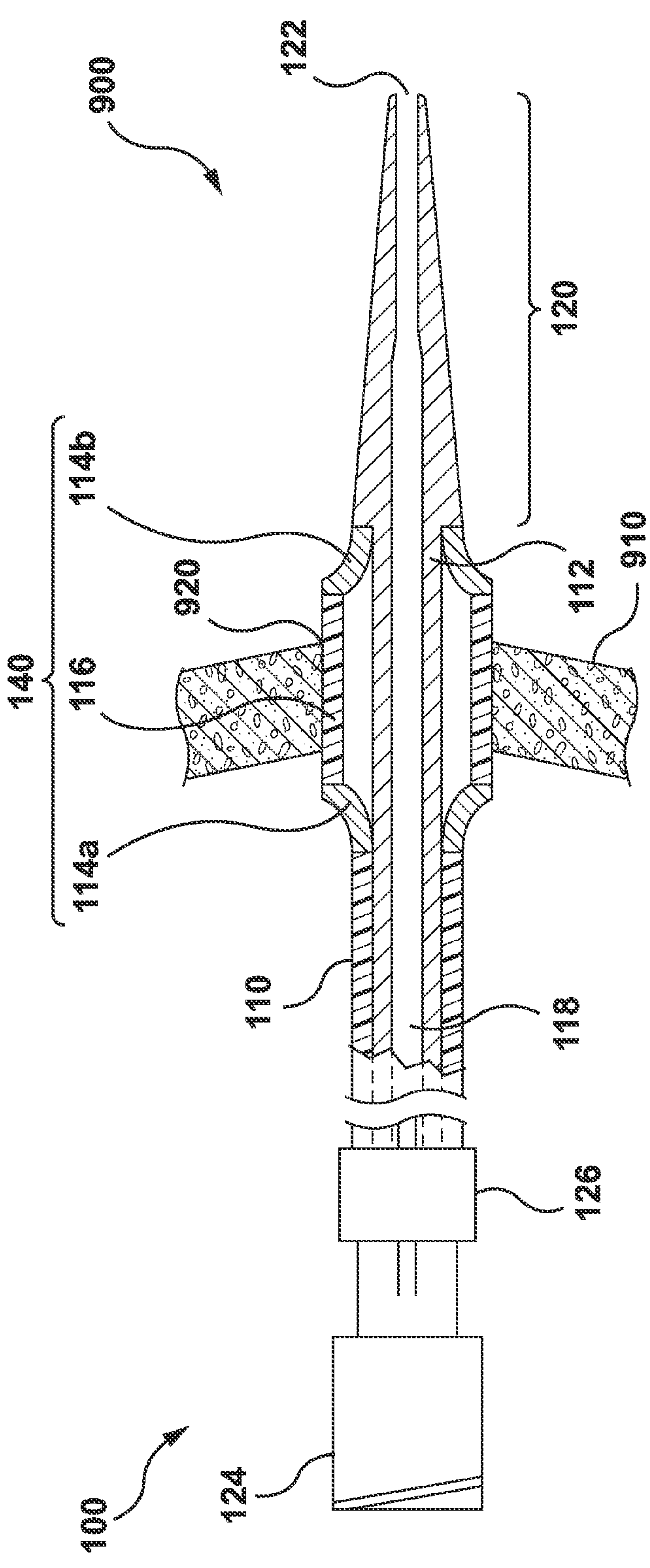
FIG. 4D depicts a partial cross section view of an elongated introducer assembly with an expanded distal expansion portion spanning a puncture hole in a tissue wall.

With reference to FIG. 4D, the same embodiment is shown as in FIG. 1A, and a procedural continuation from FIG. 4C is shown. The outer sliding shaft 110 has been advanced over the inner shaft 112 via the outer sliding shaft advancer 126 causing buckling at the first distal buckling member 114*a* and the second distal buckling member 114*b*. Buckling of the first distal buckling member 114*a* and the second distal buckling member 114*b* causes the expansion member 116 to elevate from the surface of the inner shaft 112 and thereby creates radial expansion of the elongated introducer assembly 100 at the distal expansion portion 140. The radial expansion at the distal expansion portion 140 causes expansion of the puncture hole 920 as the tissue comprising the tissue wall 910 accommodates the increased outer diameter of the elongated introducer assembly 100 at the distal expansion portion 140.

Figure 4E:
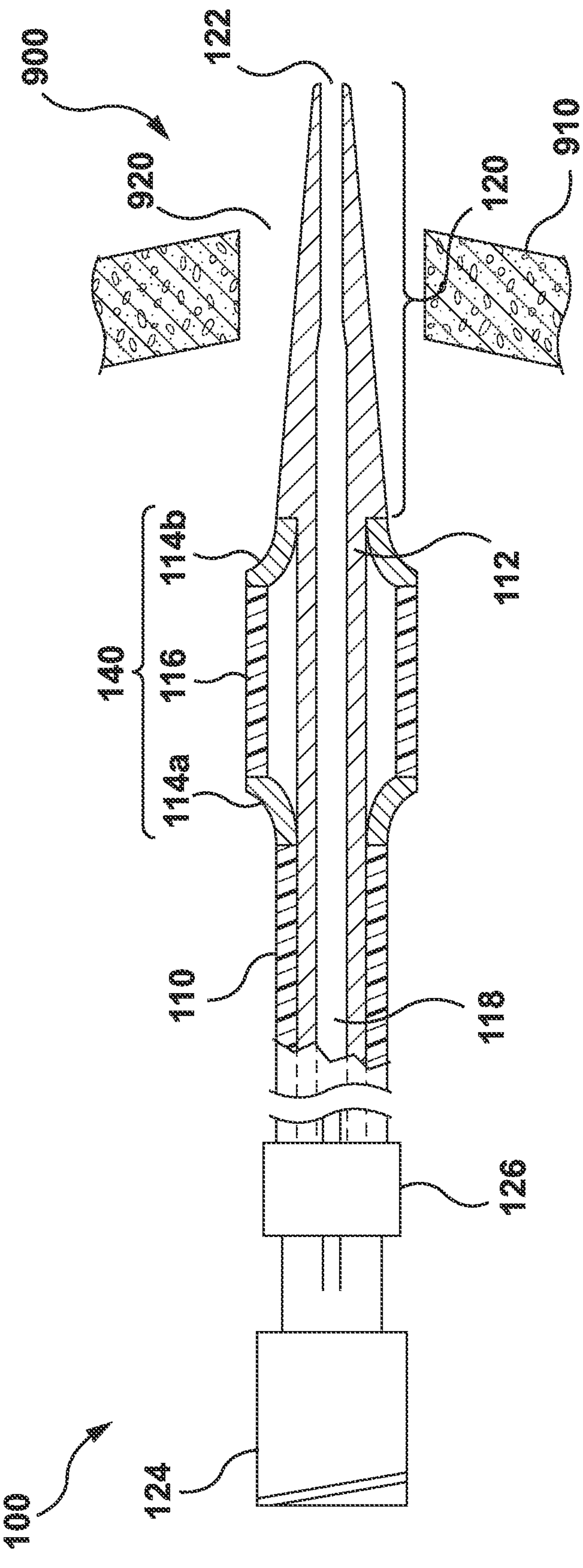
FIG. 4E depicts a partial cross section view of an elongated introducer assembly with an expanded distal expansion portion being removed from an expanded puncture hole in a tissue wall.

With reference to FIG. 4E, the same embodiment is shown as in FIG. 1A, and a procedural continuation from FIG. 4D is shown. The elongated introducer assembly 100 is retracted from the puncture hole 920 and the distal expansion portion 140 no longer spans the puncture hole 920. As a result of the radial expansion of the distal expansion portion 140 in the previous procedural step, the puncture hole 920 is expanded to a greater extent than that shown in the procedural step demonstrated in FIG. 4C.

Figure 5A:
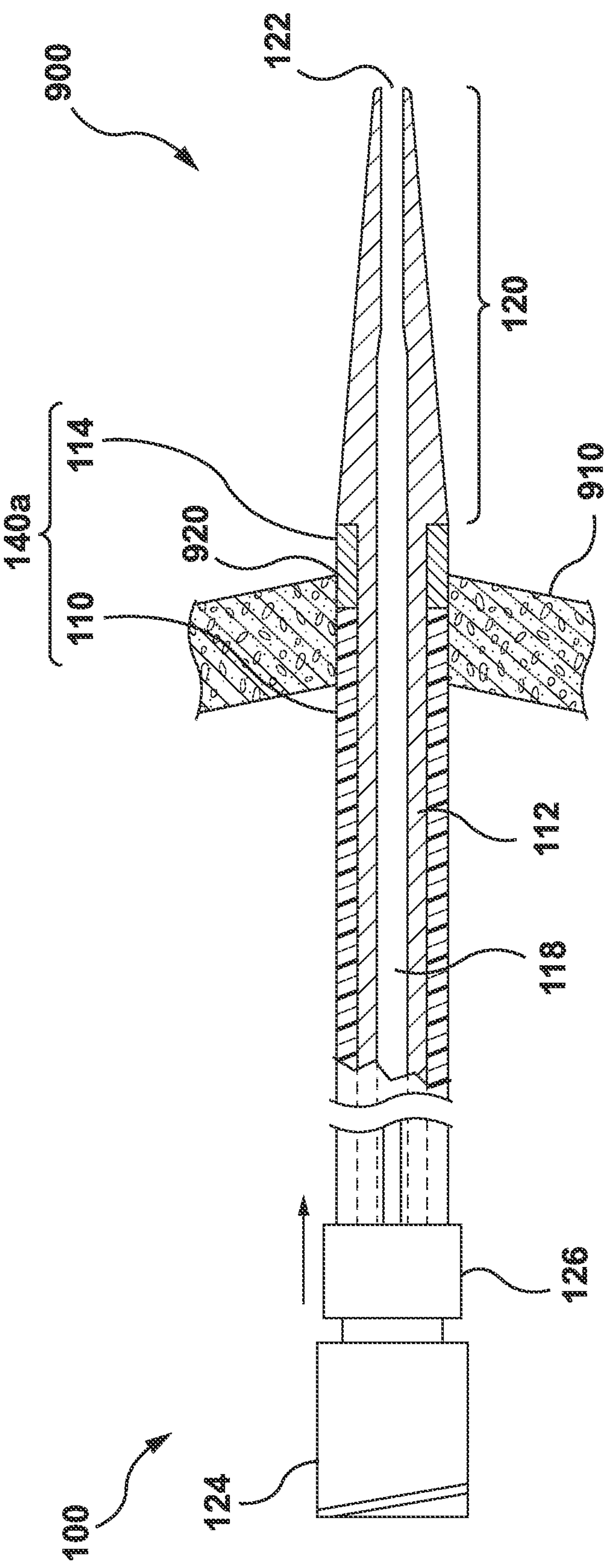
FIG. 5A depicts a partial cross section view of an elongated introducer assembly with a distal expansion portion spanning a puncture hole in a tissue wall.

With reference to FIG. 5A, the same embodiment is shown as in FIG. 2A. The distal tip 122 and distal end 120 have been advanced through the puncture hole 920 and the distal expansion portion 140*a* spans the puncture hole 920.

Figure 5B:
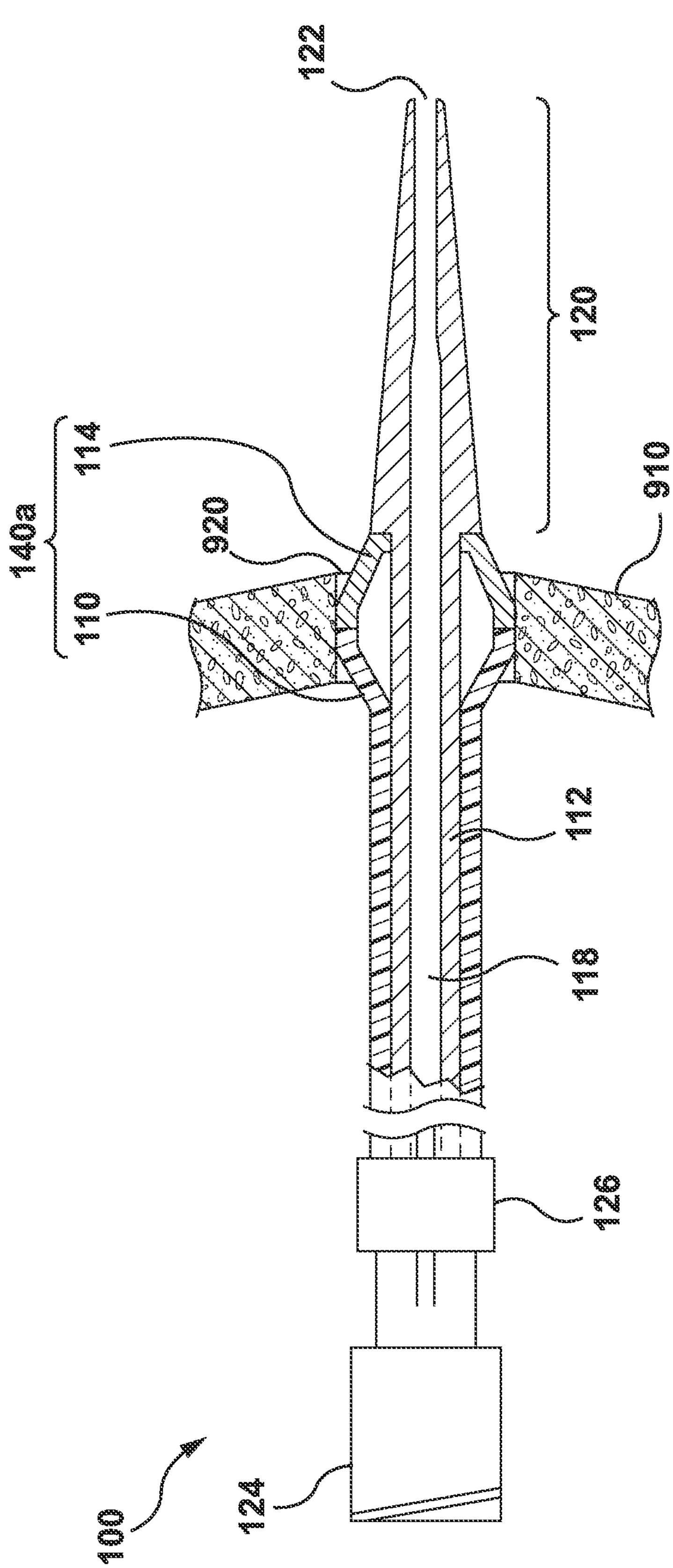
FIG. 5B depicts a partial cross section view of an elongated introducer assembly with an expanded distal expansion portion spanning a puncture hole in a tissue wall.

With reference to FIG. 5B, the same embodiment is shown as in FIG. 2A, and a procedural continuation from FIG. 5A is shown though now shown in an actuated position whereby the distal expansion portion 140*a* is radially displaced outwardly while within patient tissue (e.g., fossa ovalis). The outer sliding shaft 110 has been advanced over the inner shaft 112 via the outer sliding shaft advancer 126 causing buckling at the distal buckling member 114 and a distal portion of the outer sliding shaft 110 thereby creating radial expansion of the distal expansion portion 140*a* and an increase in the outer diameter of the elongated introducer assembly 100 at the distal expansion portion 140*a*. The radial expansion at the distal expansion portion 140*a* causes expansion of the puncture hole 920 as the tissue comprising the tissue wall 910 accommodates the increased outer diameter of the elongated introducer assembly 100 at the distal expansion portion 140*a*.

Figure 6A:
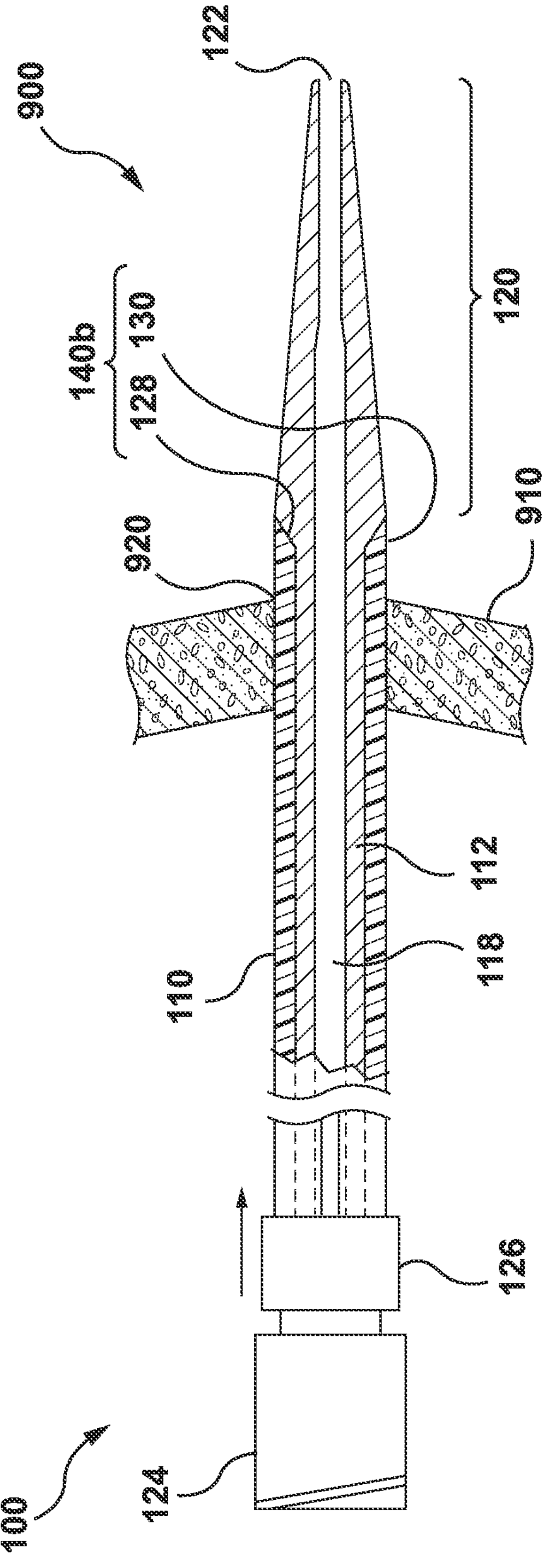
FIG. 6A depicts a partial cross section view of an elongated introducer assembly with a distal expansion portion protruding through a puncture hole in a tissue wall.

With reference to FIG. 6A, the same embodiment is shown as in FIG. 3A. The distal expansion portion 140*b* is comprised of a pre-defined sloping geometry 128 on the inner shaft 112 and a plurality of split distal outer shaft segments 130 that are contiguous with the outer sliding shaft 110. The distal tip 122, distal end 120, and distal expansion portion 140*b* have been advanced through the puncture hole 920.

Figure 6B:
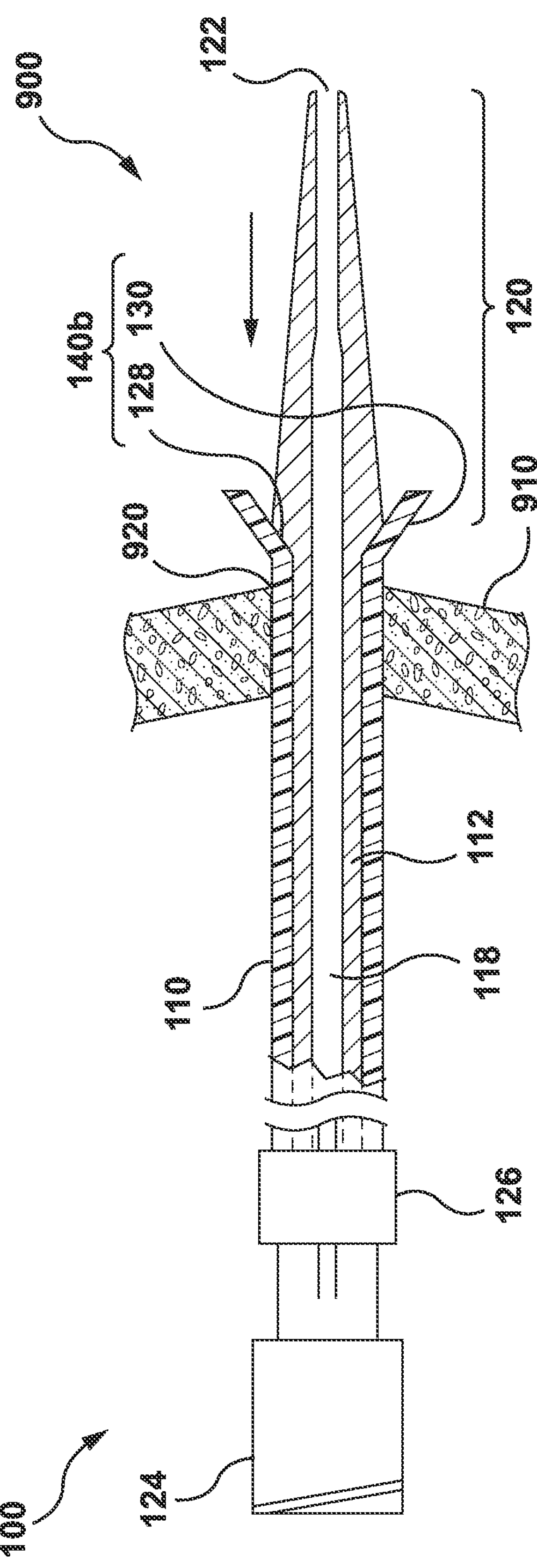
FIG. 6B depicts a partial cross section view of an elongated introducer assembly with an expanded distal expansion portion protruding through a puncture hole in a tissue wall.

With reference to FIG. 6B, the same embodiment is shown as in FIG. 3A, and a procedural continuation from FIG. 6A is shown while in an actuated position whereby the distal expansion portion 140*b* is radially displaced outwardly while adjacent patient tissue (e.g., fossa ovalis). The outer sliding shaft 110 has been advanced over the inner shaft 112 via the outer sliding shaft advancer 126 causing traversal of the plurality of split distal outer shaft segments 130 over the pre-defined sloping geometry 128 and a resultant radial expansion of the distal expansion portion 140*b* and an increase in outer diameter of the elongated introducer assembly 100 at the distal expansion portion 140*b*.

Figure 6C:
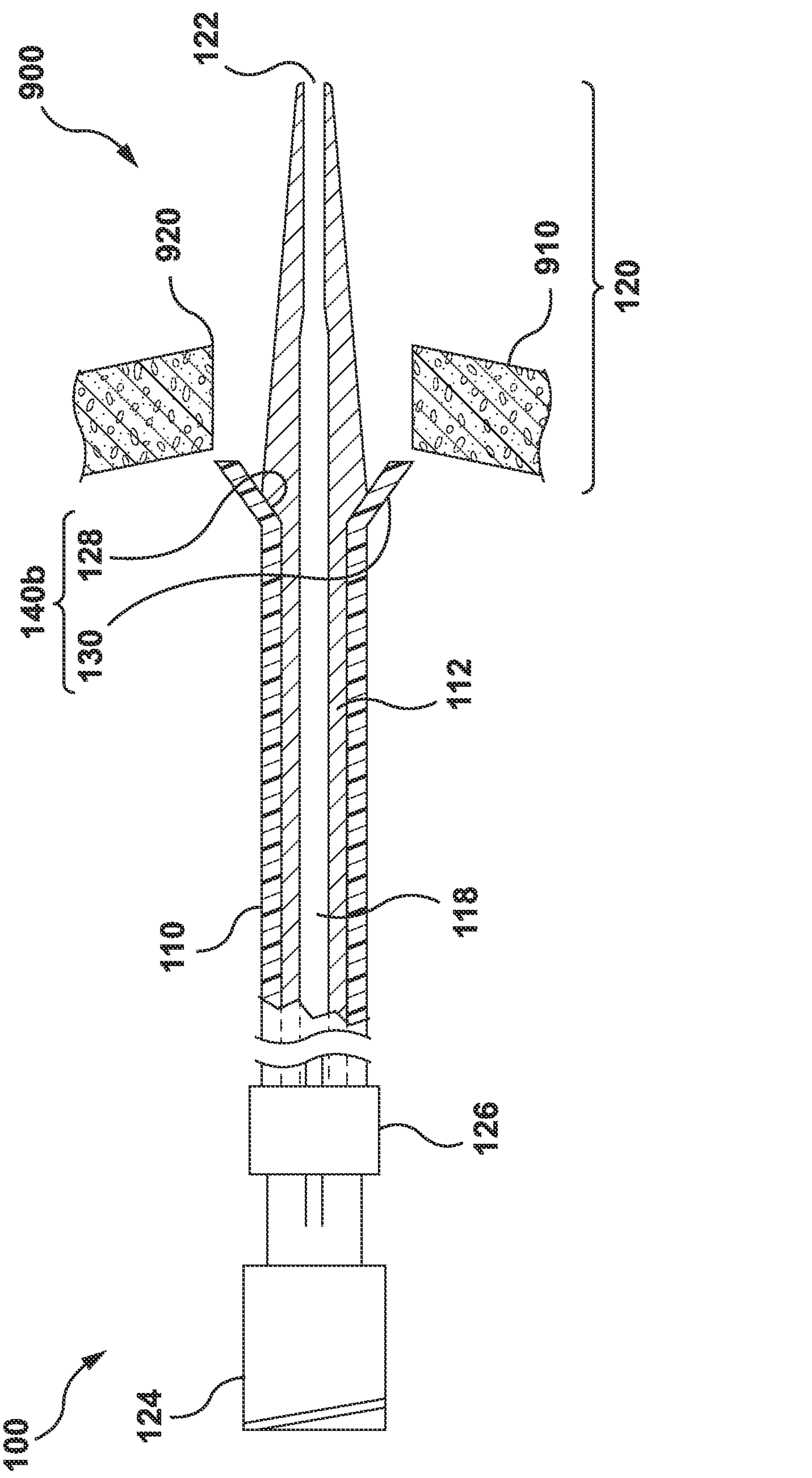
FIG. 6C depicts a partial cross section view of an elongated introducer assembly with an expanded distal expansion portion being removed from an expanded puncture hole in a tissue wall.

With reference to FIG. 6C, the same embodiment is shown as in FIG. 3A, and a procedural continuation from FIG. 6B is shown while in the actuated position. The elongated introducer assembly 100 is retracted from the puncture hole 920 and the distal expansion portion 140*b* in an expanded configuration has passed through the puncture hole 920. Passage of the distal expansion portion 140*b* through the puncture hole 920 results in an expansion of the puncture hole 920 as the tissue comprising the tissue wall 910 accommodates the outer diameter of the distal expansion portion 140*b*.

The embodiment(s) of the invention described above is(are) intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An apparatus for expanding patient tissue, the apparatus comprising:

an elongated introducer assembly configured to be maneuvered toward and positioned proximate to a puncture hole of a tissue wall;

the elongated introducer assembly including a distal end, an inner shaft, and an outer sliding shaft;

the outer sliding shaft being concentrically situated and longitudinally movable relative to the inner shaft; and a distal expansion portion contiguous with the outer sliding shaft, the distal expansion portion comprised of a pre-defined sloping geometry on the inner shaft and one or more split distal outer shaft segments on the outer sliding shaft;

wherein selective linear movement of the outer sliding shaft relative to the inner shaft forces the distal expansion portion against the distal end and actuates radial expansion of the distal expansion portion.

2. The apparatus of claim 1, wherein the distal expansion portion is comprised of one or more distal buckling members that are lower in stiffness than the outer sliding shaft.

3. The apparatus of claim 1, wherein the distal expansion portion is comprised of an expansion member and one or more distal buckling members.

4. The apparatus of claim 3, wherein the expansion member is a segment of the outer sliding shaft that is adjacent to the one or more distal buckling members.

5. The apparatus of claim 3, wherein the one or more distal buckling members is lower in stiffness than the outer sliding shaft and the expansion member.

6. The apparatus of claim 2, wherein the one or more distal buckling members is comprised of nitinol.

7. The apparatus of claim 2, wherein the one or more distal buckling members is formed by laser-cutting or any other material-removal process.

8. The apparatus of any claim 2, wherein the one or more distal buckling members is formed by flattening.

9. The apparatus of claim 3, wherein the one or more distal buckling members is comprised of a polymer material.

10. The apparatus of claim 1, wherein the outer sliding shaft is selectively moved relative to the inner shaft via an outer sliding shaft advancer.

11. The apparatus of claim 1, wherein the elongated introducer assembly includes indicators along the length of the elongated introducer assembly corresponding to the outer diameter of the distal expansion portion concomitant with the position of the outer sliding shaft relative to the inner shaft.

12. The apparatus of claim 1, wherein the inner shaft includes a hollow lumen.

13. The apparatus of claim 1, wherein the elongated introducer assembly includes a proximal hub.

14. The apparatus of claim 13, wherein the proximal hub has a female luer connector.

15. An apparatus for expanding patient tissue, the apparatus comprising:

an elongated introducer assembly configured to be maneuvered toward and positioned proximate to a puncture hole of a tissue wall;

the elongated introducer assembly having a length and including a distal end, an inner shaft, and an outer sliding shaft;

the outer sliding shaft being concentrically situated and longitudinally movable relative to the inner shaft; and a distal expansion portion contiguous with the outer sliding shaft;

wherein the elongated introducer assembly includes indicators along the length corresponding to an outer diameter of the distal expansion portion concomitant with the position of the outer sliding shaft relative to the inner shaft; and wherein selective linear movement of the outer sliding shaft relative to the inner shaft forces the distal expansion portion against the distal end and actuates radial expansion of the distal expansion portion.

16. The apparatus of claim 15, wherein the distal expansion portion is comprised of one or more distal buckling members that are lower in stiffness than the outer sliding shaft.

17. The apparatus of claim 15, wherein the distal expansion portion is comprised of an expansion member and one or more distal buckling members.

18. The apparatus of claim 17, wherein the expansion member is a segment of the outer sliding shaft that is adjacent to the one or more distal buckling members.

19. The apparatus of claim 17, wherein the one or more distal buckling members are lower in stiffness than the outer sliding shaft and the expansion member.

20. The apparatus of claim 2, wherein the one or more distal buckling members are comprised of nitinol.

* * * * *